United States Patent
Hancock et al.

(10) Patent No.: US 11,717,336 B2
(45) Date of Patent: Aug. 8, 2023

(54) ELECTROSURGICAL GENERATOR FOR DELIVERY OF DIFFERENT TYPES OF ENERGY TO BIOLOGICAL TISSUE

(71) Applicant: Creo Medical Limited, Monmouthshire (GB)

(72) Inventors: Christopher Paul Hancock, Bath (GB); Malcolm White, Chepstow (GB); John Bishop, Chepstow (GB); Ilan Wyn Davies, Chepstow (GB); Christopher Duff, Chepstow (GB); George Hodgkins, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 381 days.

(21) Appl. No.: 16/961,149

(22) PCT Filed: Mar. 8, 2019

(86) PCT No.: PCT/EP2019/055914
§ 371 (c)(1),
(2) Date: Jul. 9, 2020

(87) PCT Pub. No.: WO2019/185331
PCT Pub. Date: Oct. 3, 2019

(65) Prior Publication Data
US 2020/0397497 A1    Dec. 24, 2020

(30) Foreign Application Priority Data
Mar. 29, 2018 (GB) .................................. 1805124

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/14* (2013.01); *A61B 18/1815* (2013.01);
(Continued)

(58) Field of Classification Search
CPC ............ A61B 18/1206; A61B 18/1445; A61B 2018/00642; A61B 2018/00702;
(Continued)

(56) References Cited

U.S. PATENT DOCUMENTS 6,246,905 B1 * 6/2001 Mogul .................... A61B 50/13
  607/3
2004/0115784 A1 * 6/2004 Dzekunov .............. C12M 35/02
  435/173.6
(Continued)

FOREIGN PATENT DOCUMENTS

EP          3248561 A1    11/2017
WO    WO 2008/090444 A1    7/2008
(Continued)

OTHER PUBLICATIONS

Jiang, "A Review of Basic to Clinical Studies of Irreversible Electroporation Therapy", Jan. 2015, IEEE Transactions on Biomedical Engineering, pp. 4-20 (Year: 2015).*
(Continued)

*Primary Examiner* — Linda C Dvorak
*Assistant Examiner* — Abigail Bock
(74) *Attorney, Agent, or Firm* — ArentFox Schiff LLP

(57) ABSTRACT

An electrosurgical generator capable of supplying energy in a waveform that causes electroporation in biological tissue. The electrosurgical generator may comprise an electroporation waveform supply unit that is integrated with an electromagnetic signal supply unit for generating microwave electromagnetic signals and radiofrequency electromagnetic signals for treatment. The electrosurgical generator may be
(Continued)

configured to deliver different types of energy along a common feed cable. The electroporation waveform supply unit comprises a DC power supply and a DC pulse generator. The DC power supply may include a DC-DC converter for up-converting a voltage output by an adjustable voltage supply. Each DC pulse may have a duration in the range 1 ns to 10 ms and a maximum amplitude in the range 10 V to 10 kV.

14 Claims, 7 Drawing Sheets

(51) Int. Cl.
*A61B 18/18* (2006.01)
*A61B 18/00* (2006.01)

(52) U.S. Cl.
CPC ............ *A61B 2018/00577* (2013.01); *A61B 2018/00589* (2013.01); *A61B 2018/00601* (2013.01); *A61B 2018/00613* (2013.01); *A61B 2018/00702* (2013.01); *A61B 2018/00761* (2013.01); *A61B 2018/128* (2013.01); *A61B 2018/1273* (2013.01); *A61B 2018/1823* (2013.01)

(58) Field of Classification Search
CPC ...... A61B 18/1482; A61B 2018/00577; A61B 2018/0063; A61B 2018/00875; A61B 2018/00767; A61B 2018/1455; A61B 18/1477; A61B 2018/00083; A61B 2018/00666; A61B 2018/00791; A61B 2018/00994; A61B 18/1233; A61B 2018/00529; A61B 2090/034; A61B 2218/002; A61B 2018/00351; A61B 2018/00654; A61B 2018/00755; A61B 2018/00761; A61B 2018/00779; A61B 2018/00892; A61B 2017/00017; A61B 2018/00023; A61B 18/20; A61B 2017/320094; A61B 2018/00077; A61B 2018/0044; A61B 2018/00607; A61B 2018/00613; A61B 2018/00726; A61B 2018/00827; A61B 2018/124; A61B 2018/1823; A61B 18/14; A61B 18/1492; A61B 2018/00708; A61B 2018/0072; A61B 2018/1253; A61B 2018/1273; A61B 34/10; A61B 90/37; A61B 2017/00526; A61B 2018/00541; A61B 2018/00732; A61B 2018/126; A61B 2018/128; A61B 18/10; A61B 18/1442; A61B 18/16; A61B 18/1815; A61B 2017/00106; A61B 2018/00434; A61B 2018/00446; A61B 2018/00494; A61B 2018/00511; A61B 2018/00565; A61B 2018/00648; A61B 2018/00714; A61B 2018/00744; A61B 2018/00833; A61B 2018/00863; A61B 2018/165; A61B 2017/00022; A61B 2017/00137; A61B 2017/0015; A61B 2018/00053; A61B 2018/00178; A61B 2018/00589; A61B 2018/1293; A61B 2505/05; A61B 2018/00136; A61B 2018/00601; A61B 2090/065; A61B 2018/0013; A61B 2018/00821; A61B 2018/00898; A61B 2018/00958; A61B 2018/1465; A61B 17/320092; A61B 18/02; A61B 18/085; A61B 2017/00026; A61B 2017/00084; A61B 2017/00398; A61B 2018/00005; A61B 2018/00101; A61B 2018/00345; A61B 2018/00678; A61B 2018/00815; A61B 2018/00839; A61B 2018/00922; A61B 2018/00946; A61B 2018/0097; A61B 2018/147; A61B 2018/1495; A61B 2090/061; A61B 2090/067; A61B 2562/12; A61B 2/164; A61B 5/1459; A61B 5/4836; A61B 2017/320095; A61B 2018/00208; A61B 2018/00982; A61B 2018/0212; A61B 2018/1266; A61B 17/1642; A61B 17/1671; A61B 17/1757; A61B 17/320068; A61B 17/3472; A61B 17/3478; A61B 17/8805; A61B 18/06; A61B 18/18; A61B 2017/00261; A61B 2017/00314; A61B 2017/00331; A61B 2018/00107; A61B 2018/0016; A61B 2018/1405; A61B 2018/1475; A61B 2018/162; A61B 2018/1807; A61B 34/30; A61B 90/98; A61B 17/320016; A61B 17/320725; A61B 17/3209; A61B 18/00; A61B 18/04; A61B 18/082; A61B 18/12; A61B 18/1447; A61B 2017/00053; A61B 2017/00203; A61B 2017/00207; A61B 2017/00216; A61B 2017/00243; A61B 2017/00247; A61B 2017/00783; A61B 2017/1139; A61B 2017/22061; A61B 2018/00011; A61B 5/283; A61B 5/339; A61B 5/361; A61B 5/6853; A61B 5/6855; A61B 5/6856; A61B 5/6857; A61B 5/7267; A61B 5/745; A61B 8/0883; A61B 8/12; A61B 90/36; A61B 90/361; A61B 1/018; A61B 10/0283; A61B 17/3421; A61B 2010/045; A61B 2017/00119; A61B 2017/00128; A61B 2017/00159; A61B 2017/00172; A61B 2017/00185; A61B 2017/0019; A61B 2017/00849; A61B 2017/00867; A61B 2017/00929; A61B 2017/320064; A61B 2018/0007; A61B 2018/00172; A61B 2018/00404; A61B 2018/00785; A61B 2018/00845; A61B 2018/00904; A61B 2018/00988; A61B 2018/1467; A61B 2018/1497; A61B 2018/167; A61B 2018/1853; A61B 2018/1869; A61B 5/0507; A61B 5/346; A61B 5/352

See application file for complete search history.

(56) References Cited

U.S. PATENT DOCUMENTS

| | | | |
|---|---|---|---|
| 2006/0142688 A1 | 6/2006 | Kon et al. | |
| 2015/0105701 A1* | 4/2015 | Mayer | A61N 7/02 601/3 |
| 2015/0320481 A1* | 11/2015 | Cosman, Jr. | A61B 34/10 606/35 |
| 2017/0333109 A1* | 11/2017 | Gilbert | A61B 18/1206 |

FOREIGN PATENT DOCUMENTS

| | | |
|---|---|---|
| WO | WO 2010/068795 A2 | 6/2010 |
| WO | WO 2017/116796 A1 | 7/2017 |
| WO | WO 2018/005377 A1 | 1/2018 |

OTHER PUBLICATIONS

International Preliminary Report of Patentability issued by the International Searching Authority in corresponding International Patent Application No. PCT/EP2019/055914, dated May 28, 2020.

(56) References Cited

OTHER PUBLICATIONS

International Search Report and the Written Opinion issued by the International Searching Authority in corresponding International Patent Application No. PCT/EP2019/055914, dated May 8, 2019.
Search Report issued by the United Kingdom Patent Office in corresponding British Application No. 1805124.3, dated Sep. 14, 2018.

* cited by examiner

ELECTROSURGICAL GENERATOR FOR DELIVERY OF DIFFERENT TYPES OF ENERGY TO BIOLOGICAL TISSUE

CROSS-REFERENCE TO RELATED APPLICATIONS

This application is a National Stage entry of International Application No. PCT/EP2019/055914, filed on Mar. 8, 2019, which claims priority to British Patent Application No. 18015124.3, filed on Mar. 29, 2018. The disclosures of the priority applications are hereby incorporated in their entirety by reference.

FIELD OF THE INVENTION

The invention relates to an electrosurgical system for delivering electrical or electromagnetic energy in a plurality of modalities to cause different effects on biological tissue at a treatment site. In particular, the invention relates to an electrosurgical generator for selective supplying energy with different modalities along a common feed cable, which may be capable of being introduced through an instrument channel of a surgical scoping device (e.g. endoscope or bronchoscope) to treat biological tissue in a minimally invasive manner.

BACKGROUND TO THE INVENTION

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length.

It is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

GB 2 522 533 discloses an isolating circuit for an electrosurgical generator arranged to produce radiofrequency (RF) energy and microwave energy for treating biological tissue. The isolating circuit comprises a tunable waveguide isolator at a junction between the microwave channel and signal combiner, and can include a capacitive structure between a ground conductor of the signal combiner and a conductive input section of the waveguide isolator to inhibit coupling of the RF energy and leakage of the microwave energy.

SUMMARY OF THE INVENTION

At its most general, the present invention proposes an electrosurgical generator capable of supply energy in a waveform that is capable of causing electroporation in biological tissue. The electrosurgical generator may comprise an electroporation waveform supply unit that is integrated with means for generating microwave electromagnetic signals and radiofrequency electromagnetic signals for treatment. The electrosurgical generator may be configured to deliver different types of energy along a common feed cable. A single generator may thus be used as the source of energy of different types of treatment. This can be advantageous in terms of minimising the equipment needed in a treatment suite.

The electroporation waveform may comprise one or more high voltage energy pulses configured to open pores in cell membranes. The invention may be used in a scenario where a therapeutic agent is present at a treatment site, whereby opening pores in the cell membrane facilitates or enables the therapeutic agent to enter the cells. In other words, the invention may be used in conventional electroporation procedures.

Alternatively or additionally, the energy for electroporation may be configured to permanently open pores, thereby to cause irreversible disruption to the cell membrane causing the cells to die. In other words, the instrument can be used for irreversible electroporation (IRE).

According to the invention, there is provided an electrosurgical generator comprising: an electromagnetic signal supply unit for generating radiofrequency (RF) or microwave energy; an output port configured to be connectable to a probe for delivering the RF or microwave energy from a distal end thereof; a feed structure for conveying the RF or microwave energy to the output port; and an electroporation waveform supply unit arranged to generate energy having an electroporation waveform for causing reversible or irreversible electroporation (IRE) of biological tissue, wherein the electroporation waveform supply unit is connected to the feed structure to convey the electroporation waveform to the output port for delivery to the probe, and wherein the feed structure comprises a common signal pathway for conveying the electroporation waveform and the RF or microwave energy to the output port. In this arrangement, the same generator can supply RF energy and/or microwave energy, e.g. for tissue cutting, ablation, haemostasis or other effects as well as the electroporation waveform for causing electroporation or IRE in tissue. IRE can be used to treat liver, prostate and pancreatic cancer. By incorporating RF and/or microwave energy into a common generator, the invention may enable the same probe to deliver RF and/or microwave energy as well. This may provide more treatment options for the practitioner during a treatment procedure. For example, the ability to perform irreversible electroporation may provide the probe with a tissue treatment modality that is focussed at the distal tip. This may in turn permit a microwave ablation modality to be used to treat a larger volume around the distal tip. In combination, the instrument can be controlled to select the volume of tissue to which energy is delivered.

The electromagnetic signal supply unit may be arranged to supply both RF energy and microwave energy, either separately or simultaneously. For example, the electromagnetic signal supply unit may comprise a radiofrequency (RF) signal generator for generating RF electromagnetic (EM) radiation having a first frequency, and a microwave signal generator for generating microwave EM radiation having a second frequency that is higher than the first frequency.

The RF energy and microwave energy may be conveyed to the common signal pathway separately. For example, the feed structure may comprise an RF channel for connecting the output port to the RF signal generator, and a microwave channel for connecting the output port to the microwave signal generator. The RF channel and microwave channel may comprise physically separate signal pathways from the RF signal generator and microwave signal generator respectively. The feed structure may include a combining circuit having a first input connected to receive the RF EM radiation from the RF channel, a second input connected to receive the microwave EM radiation from the microwave channel, and an output in communication with the first and second inputs for transferring the RF EM radiation and the microwave EM radiation to the common signal pathway.

The electroporation waveform supply unit may be connectable to the common signal pathway via the RF channel. For example, a switch may be connected on the RF channel, wherein the RF signal generator and the electroporation waveform supply unit are selectively connectable to the RF channel by the switch. The switch may be any switching device capable of transmitting high frequency (e.g. UHF) energy (corresponding to the RF energy discussed herein) as well as high voltage (e.g. up to 10 kV) pulses associated with the electroporation waveform. For example, a high frequency reed relay may be used.

The feed structure may include a waveguide isolator connected to isolate the microwave channel from the RF EM radiation. The RF channel and microwave channel may be coupled into the waveguide isolator using coaxial N-type connectors. To prevent breakdown caused by pulses in the electroporation waveform, the parts of the N-type connectors that protrude into the waveguide isolator may be surrounded by a insulating material, such as PFTE having a thickness selected to inhibit breakdown.

The electroporation waveform may comprise one or more rapid high voltage pulses. Each pulse may have a pulse width in a range from 1 ns to 10 ms, preferably in the range from 1 ns to 100 µs, although the invention need not be limited to this range. Shorter duration pulses (e.g. equal to or less than 10 ns) may be preferred for reversible electroporation. For irreversible electroporation, longer duration pulses or more pulses may be used relative to reversible electroporation.

Preferably the rise time of each pulse is equal to or less than 90% of the pulse duration, more preferably equal to or less than 50% of the pulse duration, and most preferably equal to or less than 10% of the pulse duration. For the shorter pulses, the rise time may be of the order of 100 ps.

Each pulse may have an amplitude in the range 10 V to 10 kV, preferably in the range 1 kV to 10 kV. Each pulse may be positive pulse from a ground potential, or a sequence of alternating positive and negative pulses from a ground potential.

The electroporation waveform may be a single pulse or a plurality of pulses, e.g. a period train of pulses. The waveform may have a duty cycle equal to or less than 50%, e.g. in the range 0.5% to 50%.

In one example, pulse widths of the order of 200 ms delivered in a series of 10 to 100 pulses may be used for irreversible electroporation. In one example, the electroporation waveform may comprise 10×300 µs pulses of amplitude 1.5 kV delivered three times with around 1 minute between delivery. This waveform can cause cell apoptosis or death in hepatocellular carcinoma.

The electroporation waveform may be delivered during a treatment period that is selected depending on the desired effect. For example, the treatment period may be short, e.g. less than 1 second, or a few seconds, or around 1 minute. Alternatively the treatment period may be longer, e.g. up to an hour.

The pulse generator circuit may be controllable to adapt or vary the electroporation waveform to suit the desired treatment. Thus, any of the duty cycle, pulse width and pulse amplitude may be adjustably variable.

The electroporation waveform supply unit may comprise a DC power supply, e.g. arranged to operate as a high voltage source, and a pulse generator connected to the DC power supply and configured to output one or more pulses of DC power as the electroporation waveform. The DC power supply may be independent of other power sources for the generator.

The electroporation waveform supply unit may comprise a pulse signal module connected to the pulse generator and arranged to transmit one or more pulse trigger signals to the a pulse generator, wherein the pulse generator is configured to output a pulse of DC power upon receiving a pulse trigger signal. In one example, the pulse trigger signal is used to activate a drive circuit for the pulse generator, e.g. to cause a drive signal to be supplied to the pulse generator to draw power from the DC power supply.

A duration of each pulse (e.g. a pulse width) of DC power may be set by the pulse trigger signal. The pulse signal module may be controllable to permit adjustment of the duration of each pulse of DC power, e.g. under the control of a microprocessor. The pulse trigger signals may be derived from a clock signal of the microprocessor. The duration of each pulse of DC power may be in the range 1 ns to 10 ms.

The DC power supply may comprise an adjustable voltage supply, and a DC-DC converter arranged to up-convert a voltage of the adjustable voltage supply. For example, the adjustable voltage supply may have an output voltage that is adjustable in the range 1.2 V to 5 V. The DC-DC converter may convert this into a signal having a maximum voltage amplitude that is one, two or three magnitudes higher, e.g. in the range 10 V to 10 kV, preferably equal to or greater than 400 V. An amplitude of each pulse of DC power may be controllable by setting an output voltage of the adjustable voltage supply.

The pulse generator may comprise a push-pull circuit, e.g. formed from a pair of power MOSFETs connected to draw power from the DC power supply.

The generator may be connected to a probe, e.g. via a coaxial transmission line extending from the output port. The probe may comprise an electrosurgical instrument suitable for insertion through an instrument channel in a surgical scoping device. The electrosurgical instrument may have a distal end assembly configured to output any of the RF, microwave and electroporation energy discussed herein. In one example, the distal end assembly may include a coaxial structure in which an inner conductor protrudes beyond a distal end of an outer conductor and exposed at the distal end of the probe. With this configuration, the distal end assembly formed a bipolar energy delivery structure for delivering RF energy and a microwave antenna for radiating microwave energy. Furthermore, the electroporation waveform may set up a momentary electric field between the exposed distal-most ends of the inner conductor and outer conductor. The exposed conductors may be separated by a distance in the range 1 to 3 mm. The applied field may thus have an amplitude in a preferred range between 300 V/mm to 10 kV/mm.

In this specification "microwave" may be used broadly to indicate a frequency range of 400 MHz to 100 GHz, but preferably the range 400 MHz to 60 GHz. Specific frequencies that have been considered are: 433 MHz, 915 MHz, 2.45 GHz, 3.3 GHz, 5.8 GHz, 10 GHz, 14.5 GHz and 24 GHz. The device may delivery energy at more than one of these microwave frequencies. The term "radiofrequency" or "RF" may be used to indicate a frequency between 300 kHz and 400 MHz.

Herein, the term "inner" means radially closer to the centre (e.g. axis) of the instrument channel. The term "outer" means radially further from the centre (axis) of the instrument channel.

The term "conductive" is used herein to mean electrically conductive, unless the context dictates otherwise.

Herein, the terms "proximal" and "distal" refer to the ends of the energy conveying structure further from and closer to the treatment site respectively. Thus, in use the proximal end is closer to a generator for providing the microwave energy, whereas the distal end is closer to the treatment site, i.e. the patient.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Background

Figure 1:
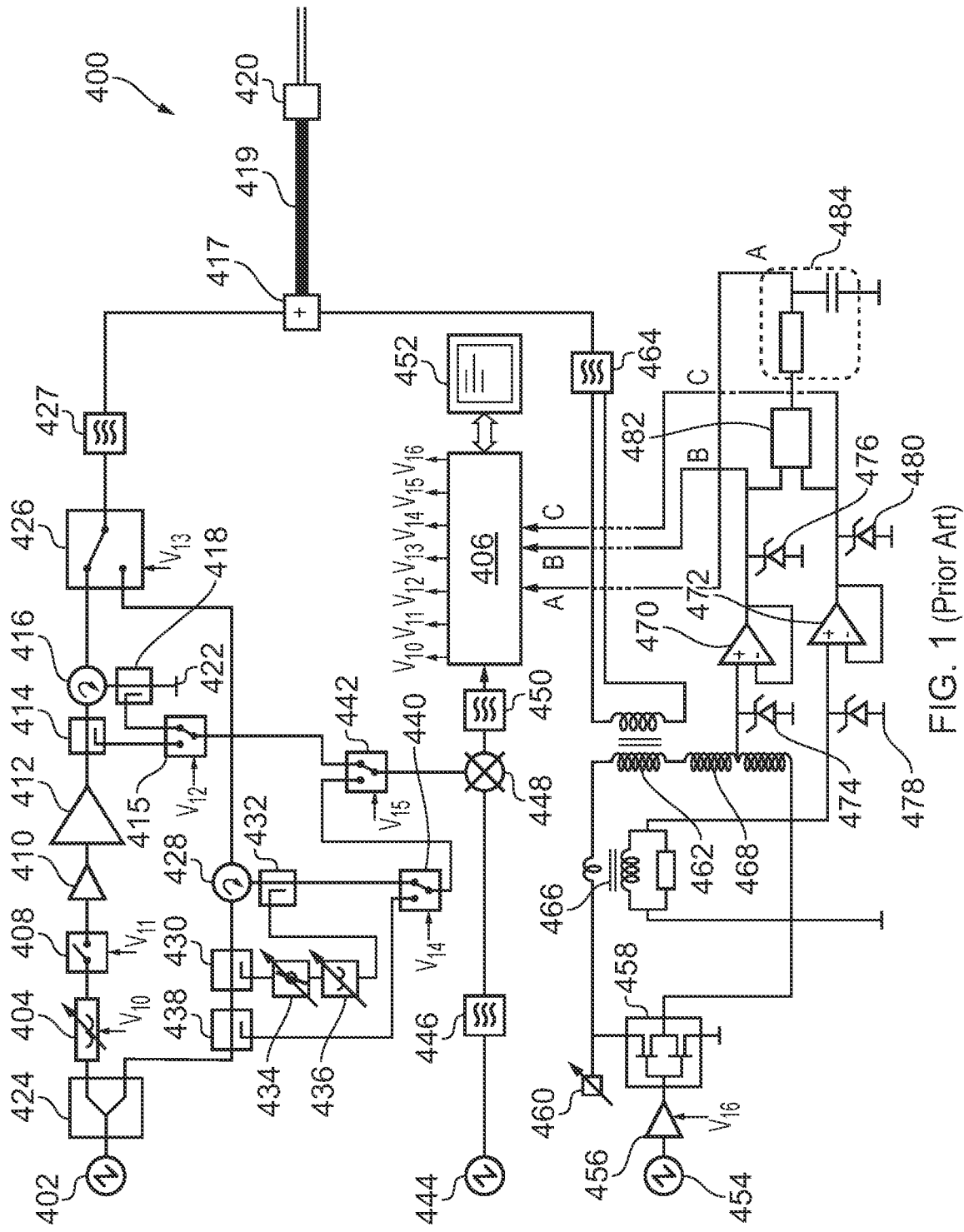
FIG. 1 is a schematic diagram of a known type of electrosurgical generator to which the present invention may be applied.

FIG. 1 shows a schematic diagram of an electrosurgical apparatus 400 such as that disclosed in GB 2 486 343 that is useful for understanding the invention. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection.

The other branch from the power splitter 424 forms a measurement channel. The measurement channel bypasses the amplifying line-up on the microwave channel, and hence is arranged to deliver a low power signal from the probe. A primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit may be used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient.

A waveguide isolator (not shown) may be provided at the junction between the microwave channel and signal combiner. The waveguide isolator may be configured to perform three functions: (i) permit the passage of very high microwave power (e.g. greater than 10 W); (ii) block the passage of RF power; and (iii) provide a high withstanding voltage (e.g. greater than 10 kV). A capacitive structure (also known as a DC break) may also be provided at (e.g. within) or adjacent the waveguide isolator. The purpose of the capacitive structure is to reduce capacitive coupling across the isolation barrier.

Figure 2:
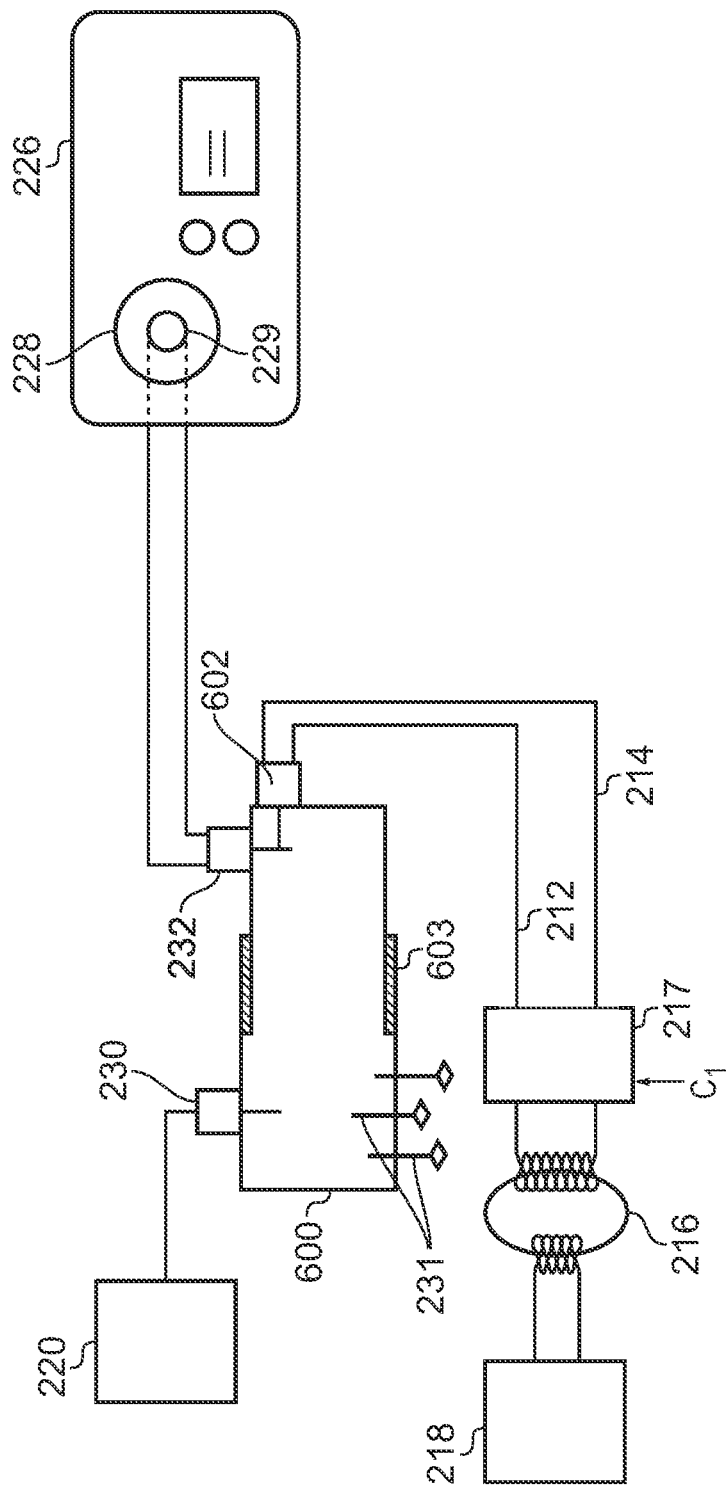
FIG. 2 is a schematic diagram of an isolating circuit that can be used in an electrosurgical generator of FIG. 1.

FIG. 2 is a schematic diagram of an isolating circuit as disclosed GB 2 522 533, which is also useful for understanding the invention. The isolating circuit forms part of a feed structure for conveying RF EM radiation from an RF signal generator 218 and microwave radiation from a microwave signal generator 220 to a probe. The probe (not shown) is connectable to an output port 228 provided in a housing 226. An insulating sleeve 229 is provided at the output port 228 of the housing to prevent a current path for connecting the grounded casing of the housing with the floating components connected to the output port 228.

The feed structure comprises an RF channel having a RF signal pathway 212, 214 for conveying the RF EM radiation and a microwave channel having a microwave signal pathway 210 for conveying the microwave EM radiation. The signal pathways for the RF EM radiation and microwave radiation are physically separate from each other. The RF signal generator is connected to the RF signal pathway 212, 214 via a voltage transformer 216. The secondary coil of the transformer 216 (i.e. on the probe side of the arrangement) is floating, so there is not direct current path between the patient and the RF signal generator 218. This means that both the signal conductor 212 and ground conductor 214 of the RF signal pathway 212, 214 are floating.

The isolating circuit comprises a waveguide isolator 600 whose insulating gap is configured to provide the necessary level of DC isolation whilst also having a capacitive reactance that is low enough at the frequency of the microwave energy to prevent leakage of the microwave energy at the gap. The gap may be 0.6 mm or more, e.g. 0.75 mm. RF energy is not able to couple between the two ends of the isolator because the diameter of the tube creates a very large inductance in series with each of the probes at the RF frequency.

The isolating circuit has a combining circuit integrated with the waveguide isolator 600. A signal conductor 212 and ground conductor 214 carrying the RF signal are connected to a coaxial RF connector 602 (RF feed), which introduces the RF signal into the waveguide isolator 600, from where it is conveyed out from an output port 232 towards the probe.

The isolating gap 603 is arranged to prevent the RF signal from coupling back into the input port 230. Microwave energy is prevented from coupling into the RF connector 602 by careful placement of the inner conductive rod within the waveguide isolator.

A tuning unit is incorporated into the waveguide isolator 600 in order to reduce the return loss of the line up of components. The tuning unit comprises three stubs 231 that can be adjustably inserted, e.g. screwed, into the body of the cavity.

In addition, the RF channel has an adjustable reactance 217 that is operable under the control of control signal $C_1$ to accommodate (e.g. compensate for) changes in capacitance arising from different lengths of cable used with the generator. The adjustable reactance 217 may comprise one or more of switched or electronically tunable capacitors or inductors connected in shunt or series with the RF channel.

Enhanced Treatment Capability

The present invention provides an electroporation waveform supply unit that can be integrated with the electrosurgical generator discussed above. Herein, term "electroporation waveform" is used to mean one or more very short high voltage energy pulses.

For example, each pulse may having a duration (i.e. pulse width) in the range 1 ns to 10 ms, preferably in the range 100 ns to 1 ms. The waveform preferably comprises a plurality of pulses. The duty cycle of a pulse train formed by the plurality of pulses may be equal to or less than 50%. In one example, the pulses may be delivered at a frequency of 50 Hz.

Each pulse may have a peak voltage (i.e. maximum pulse amplitude) in the range 10 V to 10 kV, preferably in the range 100 V to 10 kV, more preferably in the range 400 V to 10 kV.

The electroporation waveform may be configured to cause reversible or irreversible electroporation (IRE) of biological tissue at a treatment site.

As discussed below, the electroporation waveform supply unit can be arranged to deliver the electroporation waveform through the same signal pathway as the microwave energy and RF energy. Consequently, the invention may provide a generator that is capable of selectively delivering any of microwave energy, RF energy and electroporation inducing energy to a single instrument. As such, the invention may contribute towards a multimodal electrosurgical system in which a single generator unit can supply energy for a wide range of treatment types. For example, it is known that microwave energy and RF energy can be used for tissue resection or ablation and haemostasis. Moreover, it is known also to deliver gas through an instrument to a treatment site whereby the RF and/or microwave can be used to strike a thermal or non-thermal plasma for tissue sterilization or other treatment. The present invention may augment those treatment modalities by providing an electroporation effect. Other functionalities may also be integrated into the system, e.g. cryoablation techniques, ultrasound cutting, etc.

Figure 3:
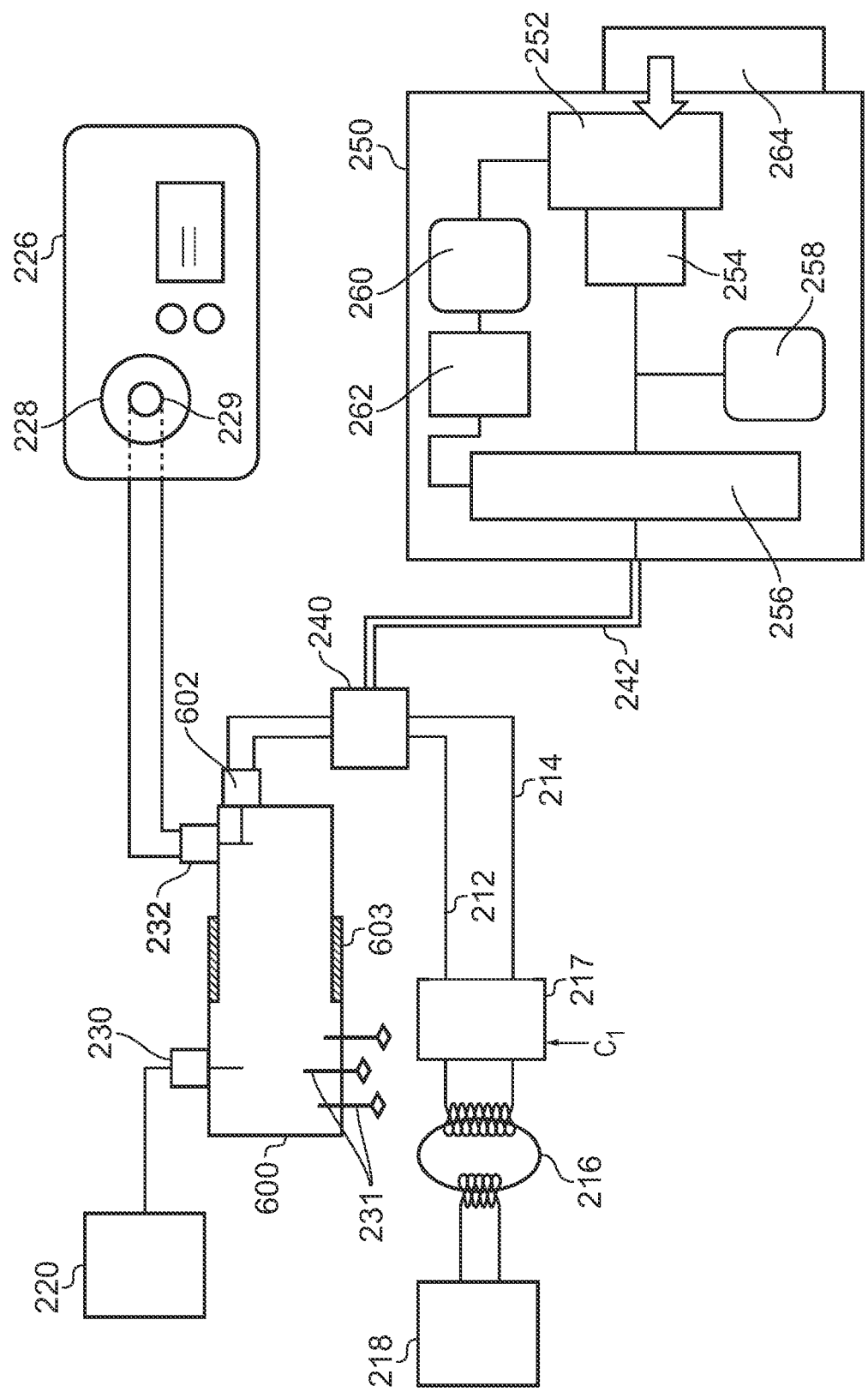
FIG. 3 is a schematic diagram of an electrosurgical generator having an electroporation waveform supply unit that is an embodiment of the invention.

FIG. 3 is a schematic diagram of an electroporation waveform supply unit 250 that is an embodiment of the invention. As shown in FIG. 3, the electroporation waveform supply unit 250 is integrated into an electrosurgical generator of the type discussed above with respect to FIGS. 1 and 2. Components in common with FIGS. 1 and 2 are given the same reference numbers and are not described again.

The electroporation waveform supply unit 250 comprises a controller 252 that is operable, e.g. via user interface 264 to control parameters of the electroporation waveform, in particular the pulse width, pulse amplitude and duty cycle (e.g. frequency of pulses in a multi-pulse train). The controller 252 includes a pulse signal module 254 that operate to send pulse trigger signals to a pulse generator 256. In one example, the pulse generator 256 can be configured as a push-pull switching circuit. The pulse generator 256 may itself receive power for operation from a dedicated power supply 258 which is independent of the power supply for the controller. This arrangement may be needed where the power requirement for driving the push-pull circuit is higher than that needed for the controller. For example, the power supply 258 may operate at 25 V, whereas the power supply for the controller may operate at 5 V.

A high voltage supply 262 is connected across the pulse generator 256. The high voltage supply 262 may comprise a DC-DC converter that up-converts an output voltage from voltage supply 260. The voltage supply 260 is connected to and controllable by the controller 252, e.g. to set the output voltage. For example, the voltage supply 260 may be an adjustable voltage supply, where the output voltage is adjustable in a range between 1.2 V to 5 V. The voltage supply 260 and the power supply 258 are DC sources, e.g. converted (rectified) from a mains power supply (not shown).

The pulse generator 256 outputs the electroporation waveform on a transmission line 242 which is connected into the RF channel discussed above by switch 240. The switch 240 may be selected to be capable of transmitting DC voltages up to 10 kV as well as being suitable for transmitting RF energy. For example, a high frequency reed relay may be used. A single-pole, dual throw (SPDT) switch may be advantageous for this component, as it permits low insertion loss switching between the RF signal and the high voltage pulse or pulses of the electroporation waveform.

With this switch, the electroporation waveform is introduced to the isolator on the RF channel. The isolator may be configured to protect the electroporation waveform supply unit 250 from microwave energy and the microwave channel from the high voltage pulses of the electroporation waveform.

To prevent breakdown from occurring in the isolator due to the high voltage pulses, the conductors which protrude into the cavity of the isolator may be surrounding by an insulating sleeve (e.g. made from PTFE or the like).

The waveguide isolator 600 shown in FIG. 2 may be designed primarily to combine a microwave signal at 5.8 GHz and an RF signal at 400 kHz, whilst also isolating the output line from being earthed through the microwave channel, and enabling independent grounding of the RF channel.

The following discussion considers the behaviour of the isolator for three type of electroporation waveform:
(i) 300 ns pulse with 1 kV amplitude and 30 ns risetime
(ii) 10 ns pulse at 10 kV
(iii) 1 ns pulse at 10 kV The physical structure of the isolator is such that signals from 1 to 100 MHz are transmitted completely. For a 300 ns rectangular pulse the frequency spectrum will have a main lobe with the first null at $\frac{1}{300}$ GHz, or 3.3 MHz. The main lobe and the next two sidelobes of the frequency spectrum will pass through the 400 kHz side of the multiplexer, up to 10 MHz. A risetime of 35 ns would be expected to correspond with a bandwidth of 10 MHz, so this waveform will pass through the isolator substantially unimpeded.

For a 10 ns pulse the first null is at 100 MHz so 300 MHz bandwidth may be needed, to get a risetime of about 1 ns. For a 1 ns pulse the first null is at 1 GHz, so it probably needs to pass 3 GHz (to get a risetime of about 0.1 ns).

Transmission through the RF port of the isolator discussed above was tested using a Vector Network Analyser, from 50 MHz to 1 GHz.

The transmission at 50 MHz was more or less 100%, i.e. 0 dB. This fell gradually to 3 dB at about 250 or 350 MHz but rose again to about 0 dB at 1 GHz. Based on this test, the isolator is operable to effectively transmit an electroporation waveform with bandwidths up to 1.5 GHz.

Figure 4:
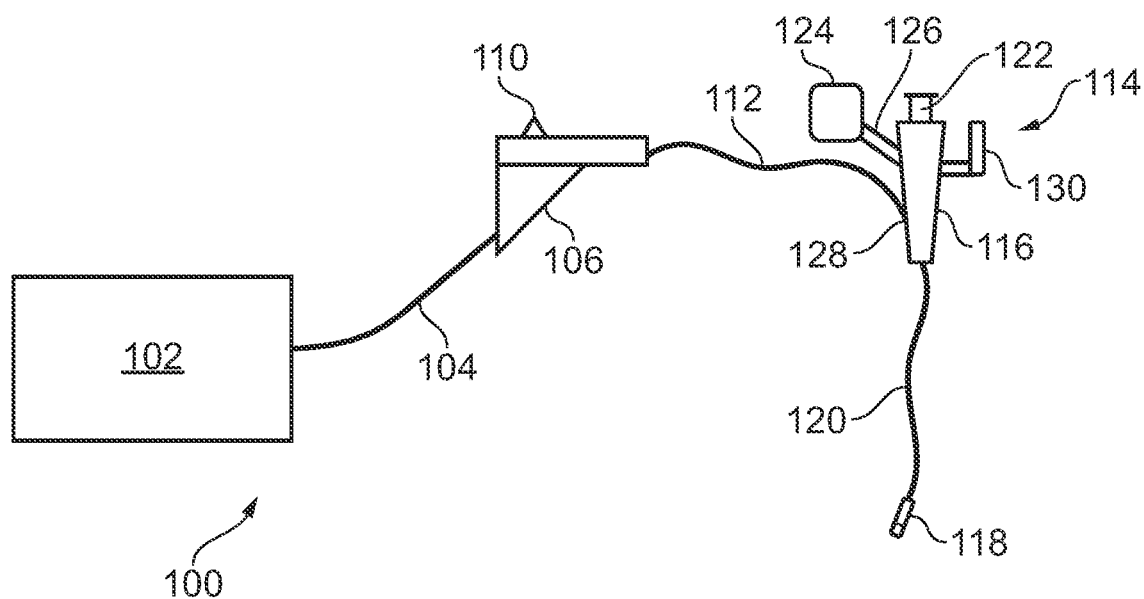
FIG. 4 is a schematic diagram showing an electrosurgical system that uses the electrosurgical generator of FIG. 3 with an instrument that is insertable through a surgical scoping device.

FIG. 4 is a schematic diagram of a complete electrosurgery system 100 that is capable of supplying RF energy, microwave energy, or the electroporation waveform discussed above to the distal end of an invasive electrosurgical instrument. The system 100 comprises a generator 102 for controllably supplying RF energy, microwave energy, and the electroporation waveform suitable for electroporation or IRE.

The generator 102 is connected to an interface joint 106 by an interface cable 104. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102 and instrument control mechanism into a single flexible shaft 112, which extends from the distal end of the interface joint 106.

The flexible shaft 112 is insertable through the entire length of an instrument (working) channel of a surgical scoping device 114, such as an endoscope, bronchoscope, gastroscope or the like.

The surgical scoping device 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is an instrument channel. Other lumens may include a channel for conveying optical radiation, e.g. to provide illumination at the distal end or to gather images from the distal end. The body 116 may include an eye piece 122 for viewing the distal end. In order to provide illumination at the distal end, a light source 124 (e.g. LED or the like) may be connected to the body 116 by an illumination input port 126.

The flexible shaft 112 has a distal assembly 118 (not drawn to scale in FIG. 1) that is shaped to pass through the instrument channel of the surgical scoping device 114 and protrude (e.g. inside the patient) at the distal end thereof. The distal end assembly includes an active tip for delivering microwave energy into biological tissue as discussed herein.

The structure of the distal assembly 118 discussed below may be designed to have a maximum outer diameter equal to or less than 2.0 mm, e.g. less than 1.9 mm (and more preferably less than 1.5 mm) and the length of the flexible shaft can be equal to or greater than 1.2 m.

The body 116 includes a power input port 128 for connecting to the flexible shaft, which comprises a coaxial cable (e.g. a conventional coaxial cable) capable of conveying the microwave energy from the generator 102 to the distal assembly 118, together with an energy conveying means (e.g. a twisted cable pair or the like) for conveying the energy for electroporation. Coaxial cables that are physically capable of fitting down the instrument channel of a surgical scoping device are available with the following outer diameters: 1.19 mm (0.047"), 1.35 mm (0.053"), 1.40 mm (0.055"), 1.60 mm (0.063"), 1.78 mm (0.070"). Custom-sized coaxial cables (i.e. made to order) may also be used.

As discussed above, it is desirable to be able to control the position of at least the distal end of the instrument cord 120. The body 116 may include a control actuator 130 that is mechanically coupled to the distal end of the instrument cord 120 by one or more control wires (not shown), which extend through the instrument cord 120. The control wires may travel within the instrument channel or within their own dedicated channels. The control actuator 130 may be a lever or rotatable knob, or any other known catheter manipulation device. The manipulation of the instrument cord 120 may be software-assisted, e.g. using a virtual three-dimensional map assembled from computer tomography (CT) images.

Figure 5:
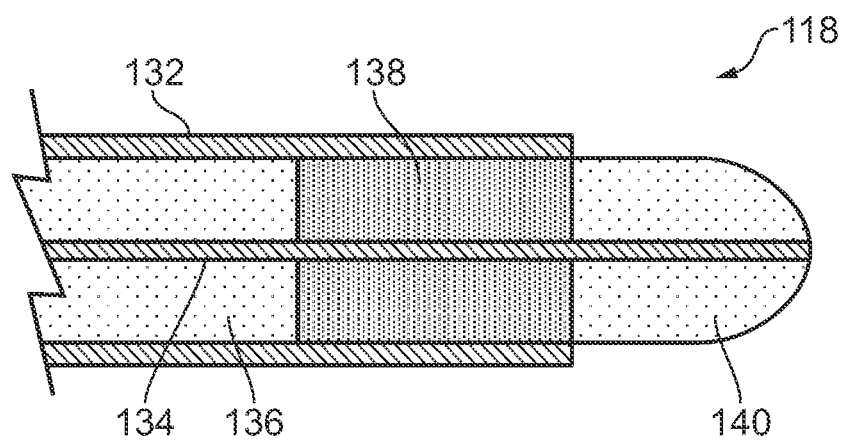
FIG. 5 is a schematic cross-sectional view of a distal end assembly of an electrosurgical instrument that is suitable for use with the present invention.

FIG. 5 shows one example of a distal end assembly 118 that can be used in the electrosurgical system discussed above, and which is capable of delivering energy in any of the available modalities (e.g. microwave, RF and electroporation).

The distal end assembly 118 comprises a coaxial transmission line formed from an inner conductor 134 that is separated from an outer conductor 132 by an insulating dielectric material 136. An energy delivery structure is formed at the distalmost end of the coaxial transmission line. The energy delivery structure comprise a length of the inner conductor that extends beyond a distal end of the outer conductor. In this example the protruding length of inner conductor is surrounded by a rigid dielectric cap 140, e.g. formed from ceramic or other low loss material. The cap 140 may have a rounded end, e.g. in a dome shape or the like, so that the instrument does not present a sharp point into tissue.

At the energy delivery structure, the inner conductor and outer conductor act as active and return electrodes for emitting the RF energy and electroporation waveform, and form an antenna structure for radiating microwave energy.

The radiating tip may have an impedance selected to match with biological tissue. In order to enable energy to be transferred efficiently into the radiating tip, an impedance transformer 138 may be provided between the coaxial transmission line. The impedance transformer 138 may be a quarter wave transmission line formed using a dielectric material having a different dielectric constant from the dielectric material 136.

Figure 6:
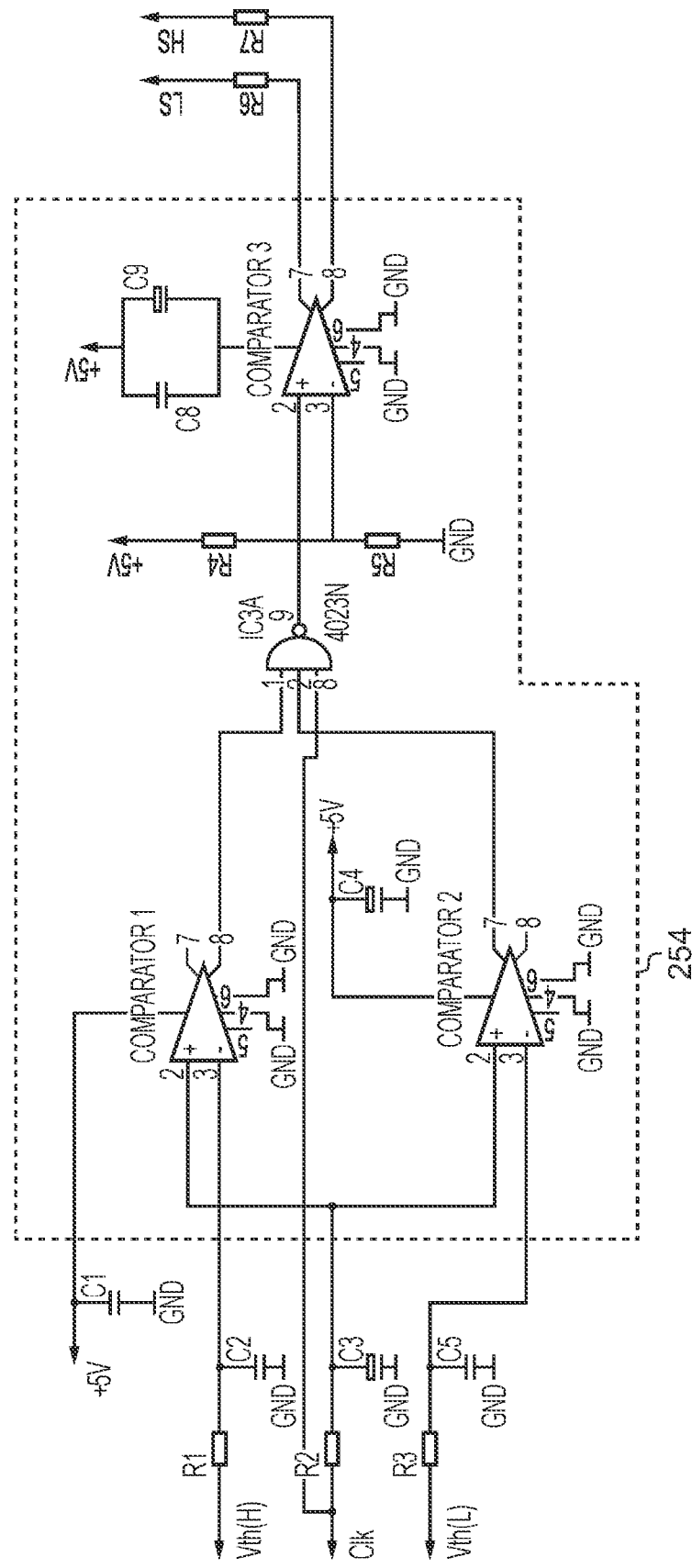
FIG. 6 is a circuit diagram for a pulse controller suitable for use in an electroporation waveform supply unit that is an embodiment of the invention.

FIG. 6 is a circuit diagram showing a specific embodiment of a pulse signal module 254 for use in a controller of the electroporation waveform supply unit discussed above. The pulse signal module 254 is arranged to output a pair of control pulses "LS", "HS" for the high and low sides of the push-pull circuit for generating the high voltage pulses, as discussed below. In this embodiment, the pulse signal module 254 is operable to set the pulse duration with reference to a clock signal "Clk" received from the controller 252, i.e. from a microprocessor that controls operation of the generator. The pulse signal module 254 comprises a window comparator circuit arranged to receive a pair of threshold voltages "Vth(H)" and "Vth(L)" which represent reference points with respect to the clock signal. A first threshold voltage Vth(H) is set to take a higher reference point from the clock signal than a second threshold voltage Vth(L). The window comparator circuit extracts short pulses from the rising and falling edges of the clock signal. These pulses are further conditioned at a fixed voltage divider comparator to generate the pair of control pulses LS, HS. The first threshold voltage Vth(H) and a second threshold voltage Vth(L) may be adjustable, e.g. at the controller, to set the pulse duration.

Figure 7:
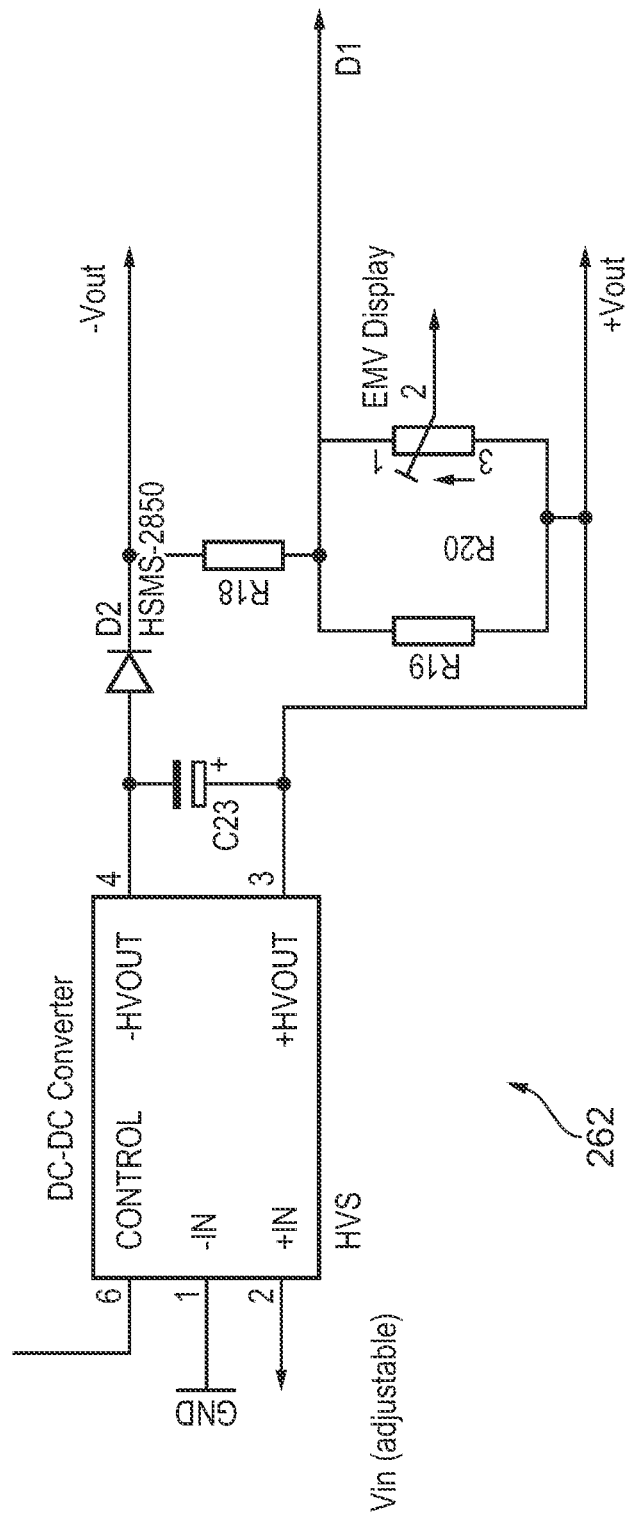
FIG. 7 is a circuit diagram for an adjustable high voltage supply suitable for use in an electroporation waveform supply unit that is an embodiment of the invention.

FIG. 7 is a circuit diagram showing an example of the high voltage supply 262. The high voltage supply 262 comprises a DC-DC convertor that is arranged to receive an input DC signal "Vin" from a separate DC supply (not shown) under the control of controller. The voltage of the input DC signal may be adjustable by the controller. The DC-DC convertor up-converts the input DC signal to create a high voltage signal across two output terminals "−Vout", "+Vout". The voltage across the output terminals is measured by extracting a voltage D1, typically at a ratio of 1000:1 (i.e. D1 is 1000th of the voltage between −Vout and +Vout). The measured voltage may be displayed on the generator. The input DC signal is controllable to enable the high voltage to be set as required. For example, Vin may be adjustable between 1.2 V and 5 V. The DC-DC convertor may be arranged to output a signal having a voltage of 1 kV or more, e.g. up to 10 kV.

Figure 8:
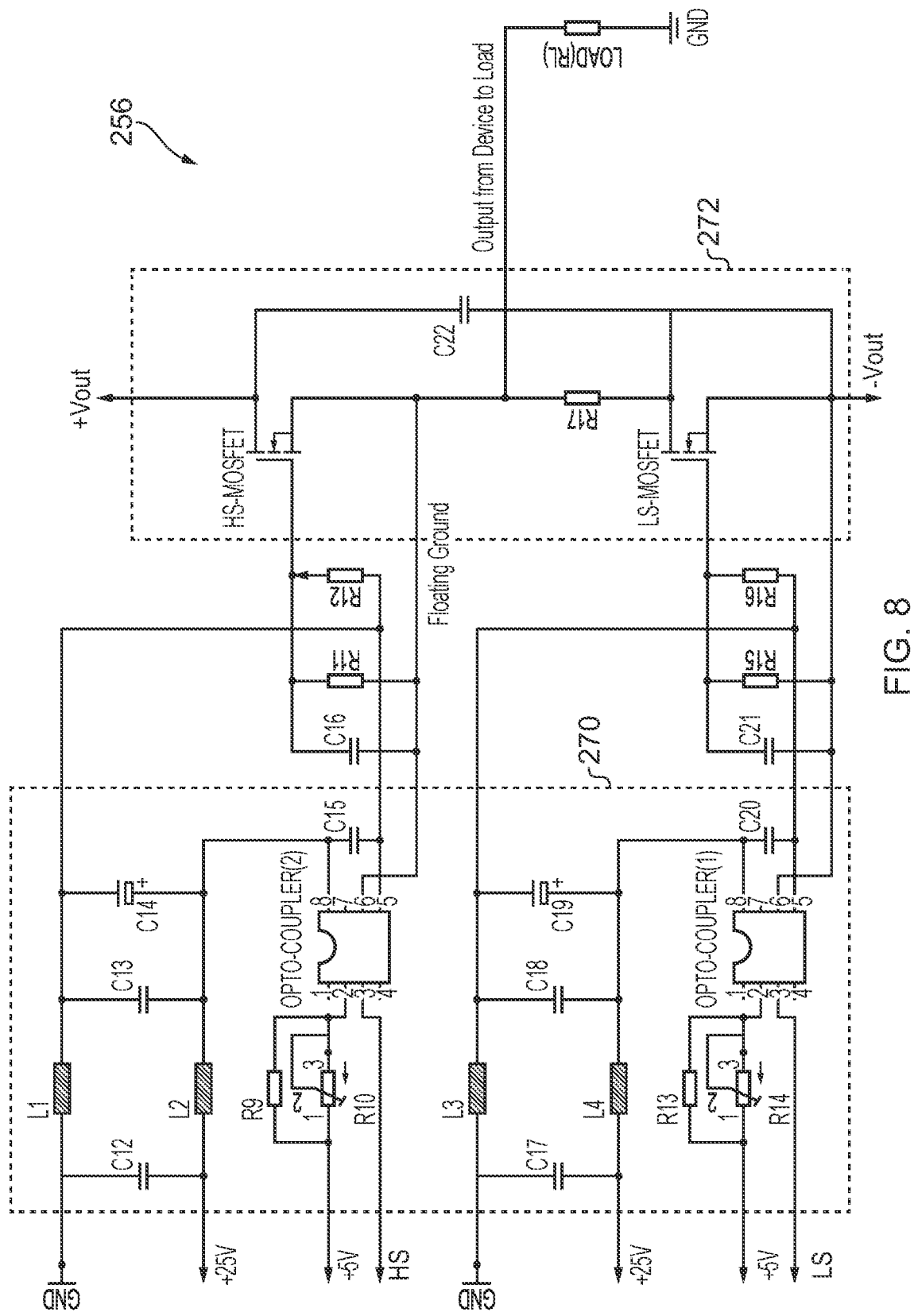
FIG. 8 is a circuit diagram for a pulse generator that is suitable for use in an electroporation waveform supply unit that is an embodiment of the invention.

FIG. 8 is a circuit diagram showing a pulse generator 256 for use in embodiments of the invention. The pulse generator 256 comprises a driver circuit 270 in which the control pulses LS, HS from the pulse signal module 254 are used to couple a driving voltage (in this example from a 25 V DC source) into the gates of a pair of power MOSFETs that are configured in a pull-pull circuit 272 to provide rapid switching of the high voltage signal between −Vout and +Vout.

The invention claimed is:

1. An electrosurgical generator comprising:
an electromagnetic signal supply unit for generating radiofrequency (RF) or microwave energy, wherein the electromagnetic signal supply unit comprises:
a radiofrequency (RF) signal generator for generating RF electromagnetic (EM) radiation having a first frequency;
a microwave signal generator for generating microwave EM radiation having a second frequency that is higher than the first frequency;
an output port configured to be connectable to a coaxial transmission line to convey the RF or microwave energy to a probe for delivering the RF or microwave energy from a distal end thereof;
a feed structure for conveying the RF or microwave energy to the output port; and
an electroporation waveform supply unit arranged to generate energy having an electroporation waveform for causing reversible or irreversible electroporation (IRE) of biological tissue,
wherein the electroporation waveform supply unit comprises:
a DC power supply that is independent of the electromagnetic signal supply unit for generating radiofrequency (RF) or microwave energy; and
a pulse generator connected to the DC power supply and configured to output one or more pulses of DC power as the electroporation waveform,
wherein the electroporation waveform supply unit is connected to the feed structure to convey the electroporation waveform to the output port for delivery to the probe, and
wherein the feed structure comprises a common signal pathway for conveying the electroporation waveform and the RF or microwave energy to the output port, and wherein the electrosurgical generator further comprises a waveguide isolator connected to isolate the electroporation waveform supply unit from the microwave signal generator.

2. The electrosurgical generator of claim 1, wherein the electroporation waveform comprises a plurality of pulses having a duty cycle equal to or less than 50%.

3. The electrosurgical generator of claim 1, wherein
the feed structure comprises an RF channel for connecting the output port to the RF signal generator, and a microwave channel for connecting the output port to the microwave signal generator, the RF channel and microwave channel comprises physically separate signal pathways from the RF signal generator and microwave signal generator respectively, and
wherein the feed structure includes a combining circuit having a first input connected to receive the RF EM radiation from the RF channel, a second input connected to receive the microwave EM radiation from the microwave channel, and an output in communication with the first and second inputs for transferring the RF EM radiation and the microwave EM radiation to the common signal pathway.

4. The electrosurgical generator of claim 3 comprising a waveguide isolator connected to isolate the microwave channel from the RF EM radiation.

5. The electrosurgical generator of claim 3, wherein the electroporation waveform supply unit is connectable to the common signal pathway via the RF channel.

6. The electrosurgical generator of claim 5 comprising a switch connected on the RF channel, wherein the RF signal generator and the electroporation waveform supply unit are selectively connectable to the RF channel by the switch.

7. The electrosurgical generator of claim 1 including a pulse signal module connected to the pulse generator and arranged to transmit one or more pulse trigger signals to the pulse generator, wherein the pulse generator is configured to output a pulse of DC power upon receiving a pulse trigger signal.

8. The electrosurgical generator of claim 7, wherein the pulse generator comprises a push-pull circuit.

9. The electrosurgical generator of claim 7, wherein a duration of each pulse of DC power is set by the pulse trigger signal.

10. The electrosurgical generator of claim 9, wherein the pulse signal module is controllable to permit adjustment of the duration of each pulse of DC power.

11. The electrosurgical generator of claim 9, wherein the duration of each pulse of DC power is in the range 1 ns to 10 ms.

12. The electrosurgical generator of claim 7, wherein the DC power supply comprises:
an adjustable voltage supply; and
a DC-DC converter for up-converting the voltage of the adjustable voltage supply,
wherein an amplitude of each pulse of DC power is controllable via the adjustable voltage supply.

13. The electrosurgical generator of claim 12, wherein a maximum amplitude of each pulse of DC power is in the range 10 V to 10 kV.

14. The electrosurgical generator of claim 13, wherein the maximum amplitude of each pulse of DC power is equal to or greater than 400 V.

* * * * *